United States Patent
Vreeke et al.

(10) Patent No.: US 8,251,920 B2
(45) Date of Patent: *Aug. 28, 2012

(54) SWING LANCE WITH INTEGRATED SENSOR

(75) Inventors: Mark S. Vreeke, Houston, TX (US); Scott L. Hoover, Goshen, IN (US); Steven C. Charlton, Osceola, IN (US); Larry D. Johnson, Elkhart, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 118 days.

This patent is subject to a terminal disclaimer.

(21) Appl. No.: 12/686,942

(22) Filed: Jan. 13, 2010

(65) Prior Publication Data

US 2010/0152617 A1 Jun. 17, 2010

Related U.S. Application Data

(63) Continuation of application No. 10/899,774, filed on Jul. 27, 2004, now Pat. No. 7,670,300.

(60) Provisional application No. 60/490,019, filed on Jul. 28, 2003.

(51) Int. Cl.
*A61B 5/00* (2006.01)
*A61B 17/14* (2006.01)
*A61B 17/32* (2006.01)
*B65D 81/00* (2006.01)

(52) U.S. Cl. ........ 600/583; 600/573; 600/576; 600/584; 606/181; 606/182

(58) Field of Classification Search .................. 600/573, 600/576, 583, 584; 606/181, 182
See application file for complete search history.

(56) References Cited

U.S. PATENT DOCUMENTS

| 4,637,403 | A |   | 1/1987  | Garcia et al. |
|-----------|---|---|---------|---------------|
| 4,643,189 | A |   | 2/1987  | Mintz |
| 4,924,879 | A | * | 5/1990  | O'Brien ................ 600/583 |
| 5,035,704 | A |   | 7/1991  | Lambert et al. |
| 5,231,993 | A |   | 8/1993  | Haber et al. |
| 5,314,441 | A |   | 5/1994  | Cusack et al. |
| 5,632,410 | A |   | 5/1997  | Moulton et al. |
| 5,723,284 | A |   | 3/1998  | Ye |
| 5,759,364 | A |   | 6/1998  | Charlton et al. |
| 5,772,677 | A |   | 6/1998  | Mawhirt et al. |
| 5,810,199 | A |   | 9/1998  | Charlton et al. |
| 5,854,074 | A |   | 12/1998 | Charlton et al. |

(Continued)

FOREIGN PATENT DOCUMENTS

WO 98/58260 12/1998

*Primary Examiner* — Sean Dougherty
(74) *Attorney, Agent, or Firm* — Nixon Peabody LLP

(57) ABSTRACT

An apparatus for lancing skin and collecting a liquid sample. The apparatus having a housing with an outer periphery and a rotatable arm having a lance to puncture the skin. A sample collection area is attached to the arm. The arm of the apparatus rotates from a first position to a second position. As the arm rotates, the lance extends beyond the housing allowing the lance to contact the user's skin and create a lance site. As the arm continues to move to the second position, the lance is brought out of contact with the user's skin and back within the housing while the collection area is brought into position. When the arm is located in the second position, the collection area is in substantially the same location as the lance site on the user's skin.

18 Claims, 3 Drawing Sheets

U.S. PATENT DOCUMENTS

| | | |
|---|---|---|
| 5,879,310 A | 3/1999 | Sopp et al. |
| 5,879,311 A * | 3/1999 | Duchon et al. ............... 600/583 |
| 5,971,941 A | 10/1999 | Simons et al. |
| 6,316,264 B1 | 11/2001 | Corey et al. |
| D456,514 S | 4/2002 | Brown et al. |
| 6,626,851 B2 | 9/2003 | Hirao et al. |
| 6,706,159 B2 | 3/2004 | Moerman et al. |
| 6,783,502 B2 | 8/2004 | Orloff et al. |
| 6,988,996 B2 | 1/2006 | Roe et al. |
| 7,582,063 B2 | 9/2009 | Wurster et al. |
| 2002/0188224 A1 | 12/2002 | Roe et al. |
| 2003/0073933 A1 | 4/2003 | Hirao et al. |
| 2003/0191415 A1 | 10/2003 | Moerman et al. |
| 2004/0039303 A1 | 2/2004 | Wurster et al. |
| 2004/0225312 A1 | 11/2004 | Orloff et al. |

* cited by examiner

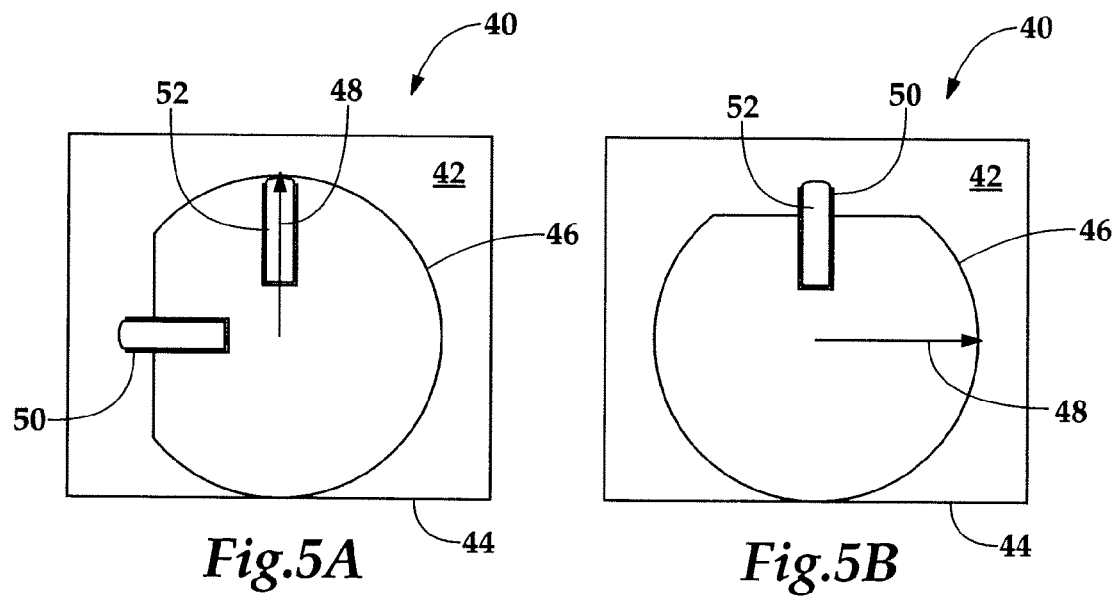
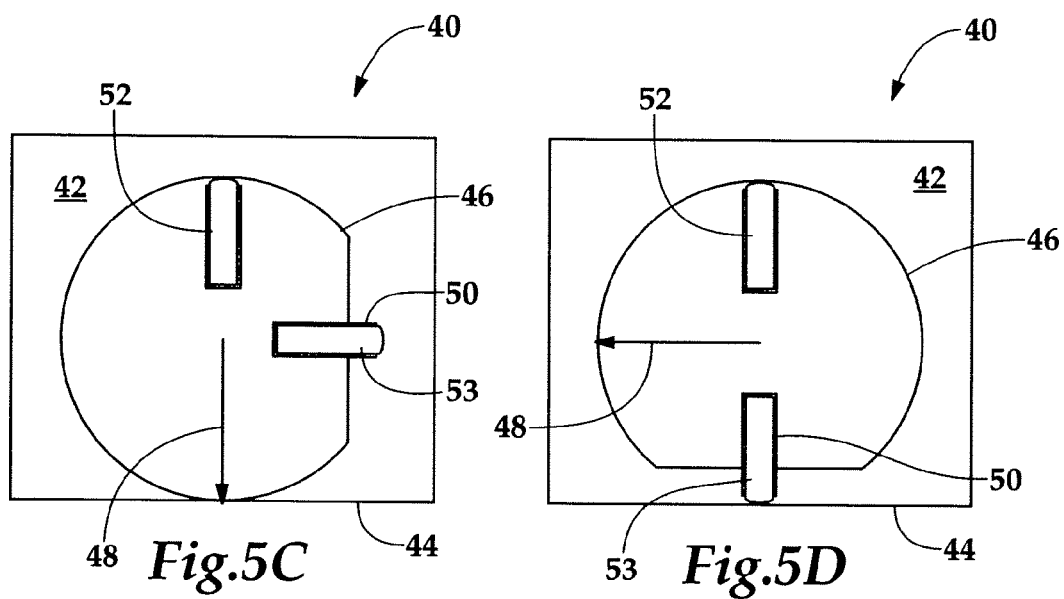

SWING LANCE WITH INTEGRATED SENSOR

CROSS-REFERENCE TO RELATED APPLICATION

This application is a continuation of allowed U.S. patent application Ser. No. 10/899,774, filed Jul. 27, 2004, that claims the benefit of the U.S. Provisional Application 60/490,019, filed on Jul. 28, 2003.

FIELD OF THE INVENTION

The present invention relates generally to body fluid monitoring devices, and more particularly to a lancing mechanism and body fluid collection system.

BACKGROUND OF THE INVENTION

It is often necessary to obtain a sample of a body fluid and perform an analysis of an analyte in that body fluid. Preferably, the obtaining of body fluid is as painless as possible, and the collection of the sample is as simple as possible. One example of a need to obtain a sample of a body fluid is in connection with a blood glucose monitoring system where a user must frequently use the system to monitor the user's blood glucose level.

Those who have irregular blood glucose concentration levels are medically required to regularly self-monitor their blood glucose concentration level. An irregular blood glucose level can be brought on by a variety of reasons including illness such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky, and confused. That person's judgment may become impaired and that person may eventually pass out. A person can also become very ill if his blood glucose level becomes too high—a condition known as hyperglycemia. Both conditions, hypoglycemia and hyperglycemia, are both potentially life-threatening emergencies.

One method of monitoring a person's blood glucose level is with a portable, hand-held blood glucose testing device. The portable nature of these devices enables the users to conveniently test their blood glucose levels wherever they may be. To check the blood glucose level, a drop of blood is obtained from the fingertip using a separate lancing device. The lancing device contains a needle lance to puncture the skin. Once the requisite amount of blood is produced on the fingertip, the blood is harvested using the blood glucose testing device. The blood is drawn inside the testing device, which then determines the concentration of glucose in the blood. The results of the test are communicated to the user via a display on the testing device.

One problem related with the prior art devices containing a separate lance and sample collection mechanism is that the user must carry both devices with him. The need to carry multiple devices opens the possibility of forgetting or losing one of the devices. If the user forgets to bring both the lance and the testing device with him, he will not be able to test his blood; adverse consequences may result.

Another problem with a monitoring system comprising a lancing device to lance the skin and a separate collection unit to collect the blood is that there is a greater chance of contaminating the sample. The user must be careful that he does not contaminate the blood drop that forms on the lance site or contaminate the collection device used. If any contamination occurs, the test result may not accurately reflect the level of the glucose present in the tested blood.

A third problem with having a device for lancing and a separate device for collection is the size of the sample needed. Users prefer to make smaller cuts, also referred to as lance sites, on their skin to produce a blood sample. A smaller lance site is usually less painful to make than a larger lance site, and should heal more quickly than a larger lance site. Generally, a smaller lance site will produce a smaller blood sample. The smaller the sample, the more important proper collection of the sample becomes. And a smaller sample requires greater precision in placing the collection device relative to the lance site. If the collection device is not properly positioned relative to the lance site on the user's skin, the requisite amount of sample may not be collected. If the requisite amount of sample is not collected an underfill condition occurs. The results of analyzing an underfill will not accurately reflect the amount of glucose present in the sample, or in the user.

Another problem with current lancing devices is that accidental lancing may occur from the exposed lance. If the lance is exposed it may come into contact with the user's skin in a location that the user did not intend to serve as a lance site. This cut may be painful and limit the available locations for a lance site.

Accordingly, there exists the need of a device that combines lancing capability and collection capability into one instrument. The combination device should be suitable for lancing skin and aligning the collection device at the lance site, collecting a small sample of blood from a small lance site on the skin, and reducing risk of accidental lance sites being formed from an exposed lance.

SUMMARY OF THE INVENTION

An apparatus for lancing skin and collecting a liquid sample, having a housing with an outer periphery. The apparatus contains a rotatable arm having a lance to puncture the skin and a sample collection chamber attached to the arm. The arm of the apparatus rotates from a first position to a second position. As the arm rotates, the lance extends beyond the housing allowing the lance to contact the user's skin and create a lance site. As the arm continues to move to the second position, the lance is brought out of contact with the user's skin and back within the housing. When the arm is located in the second position, the collection area is in substantially the same location as the lance site on the user's skin.

BRIEF DESCRIPTION OF THE DRAWINGS

Other objects and advantages of the invention will become apparent upon reading the following detailed description in conjunction with the drawings in which:

FIG. 5A shows a top view of an alternate embodiment of the present invention in which a sample collection area can be removed from the apparatus.

FIG. 5B illustrates the embodiment of FIG. 5A as a new sample collection area is being loaded into the apparatus.

FIG. 5C illustrates the embodiment of FIG. 5A as the lance is extended beyond the outer periphery of the housing of the apparatus.

FIG. 5D illustrates the embodiment of FIG. 5A with the sample collection area positioned in substantially the same position as the lance site that was made as shown in FIG. 5C.

DETAILED DESCRIPTION OF THE DRAWINGS

As discussed in the background section, the need to obtain a sample of blood and perform an analysis of that sample occurs frequently for persons with various medical conditions. Many people who suffer from conditions such as diabetes must regularly test the level of glucose contained in their blood. One way to perform this test would be with a device that combines the operation of lancing the skin and collecting the sample.

Figure 1:
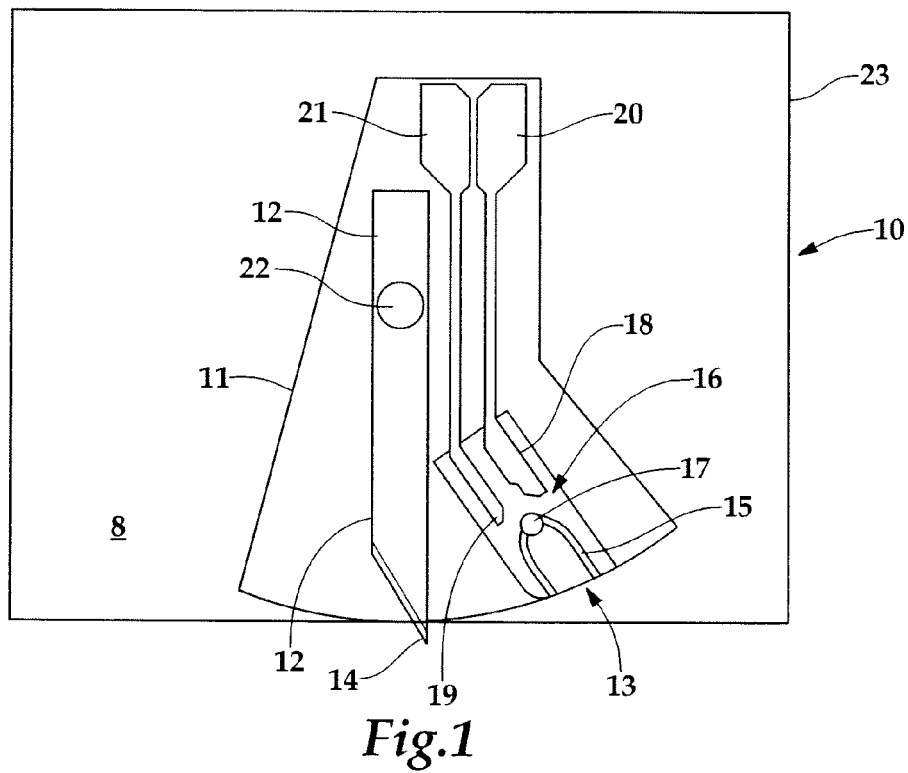
FIG. 1 is a side view of an apparatus for sampling fluid and showing a housing and a rotatable arm.

Referring now to FIG. 1, an apparatus 10 for lancing skin and collecting a liquid sample is illustrated. The apparatus 10 has a housing 8 with an outer periphery 23. A movable arm 11 is connected in the housing 8 to swing in a predefined path. Connected to movable arm 11 is a lance 12 and a sample collection area 13. As the arm 11 swings, the lance 12 is sequentially extended beyond the outer periphery 23 and retracted into housing 8.

Figure 2:
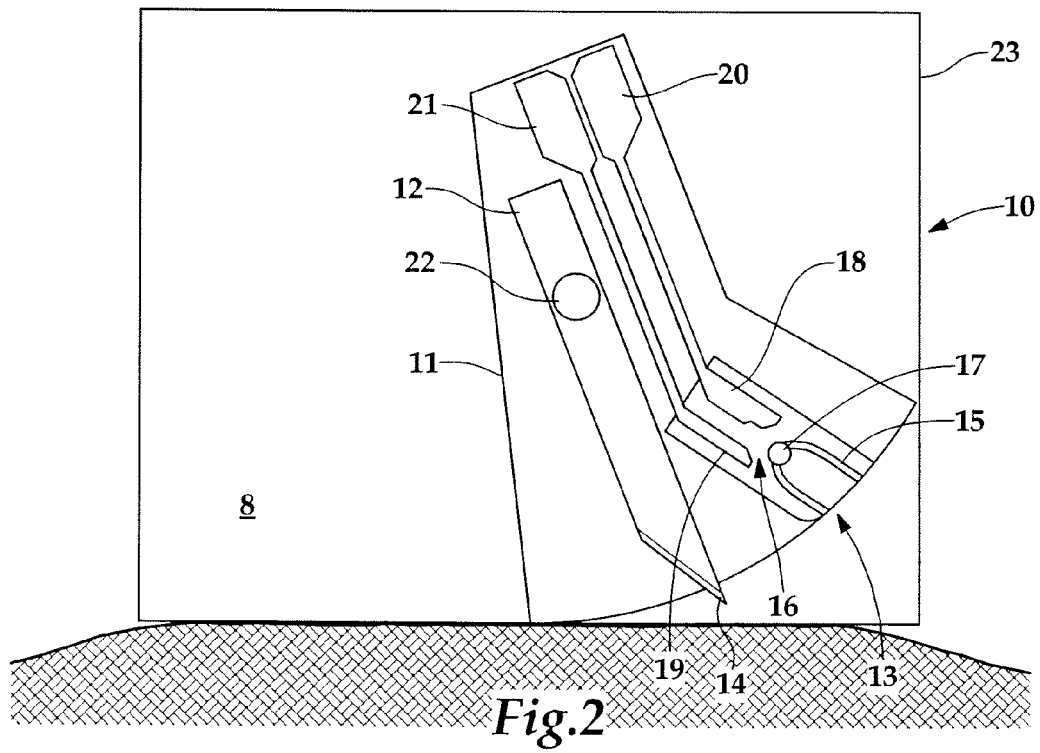
FIG. 2 is a side view of the apparatus shown in FIG. 1 with the arm in a first position with the lance in the housing.

Referring now to FIG. 2, the arm 11, which comprises the lance 12, and the collection area 13, pivots about point 22 as the arm 11 swings from a first position to a second position. The lance 12 has a sharp penetration end 14 that is capable of lancing a user, thereby creating a lance site on the skin to obtain a liquid sample for analysis. In a preferred embodiment, the lance 12 is a flat surface lying in the plane of rotation of the arm 11. The flat surface is useful to stabilize the lance 12 relatively to the arm 11. The collection area 13 is used to collect a liquid sample that forms at the lance site created by the lance 12. The second position of the arm 11 is predetermined to position the collection area 13 at the lance site created as the arm 11 rotates to the second rotation.

In one embodiment of the current invention, the collection area 13 includes a capillary channel 15 through which the sample moves as it is collected. As the sample moves up the capillary channel 15, displaced air exits from the capillary channel 15 via a vent hole 17. In the illustrated embodiment, the collection area 13 includes a biosensor 16.

When an electrochemical biosensor is used, the biosensor 16 contains a reagent designed to react with the analyte in the sample and produce a change in current. The change in current is measured across traces 18 and 19. Additional detail concerning electrochemical biosensors is found in commonly owned U.S. Pat. No. 5,759,364, which is incorporated herein by reference in its entirety. The change in current is measured by a meter coupled to terminals 20 and 21 of traces 18 and 19 coupled to electrodes (not shown) in the capillary.

The collection area 13 may be provided with the biosensor 16 having a reaction area that includes a reagent for producing a reaction with an analyte within the liquid sample 25. The reaction is indicative of the concentration of the analyte within that sample. In the case of a glucose tester, the reagent could be a mixture containing glucose oxidase and potassium ferricyanide. In one embodiment of the current invention, the biosensor is an electrochemical sensor. An optical sensor may also be used to analyze the liquid sample.

Another suitable biosensor is a colorimetric sensor; details of which is described in U.S. Pat. No. 5,723,284, which is incorporated herein by reference in its entirety.

To obtain a sample of blood, the user places the apparatus 10 on his skin 24 at a site to lance. In FIG. 2, the apparatus 10 is applied to the skin 24 of the user. The rotatable arm 11 is shown in a first position. Next, the user activates the device by for example, pressing the trigger mechanism on the apparatus 10 (not shown). Pressing the trigger releases a torsion spring (not shown) that forces the arm 11 to rotate from the first position to a second position. The arm 11 is, in the illustrated embodiment, a pendulum that swings through a predefined arc about pivot point 22.

Figure 3:
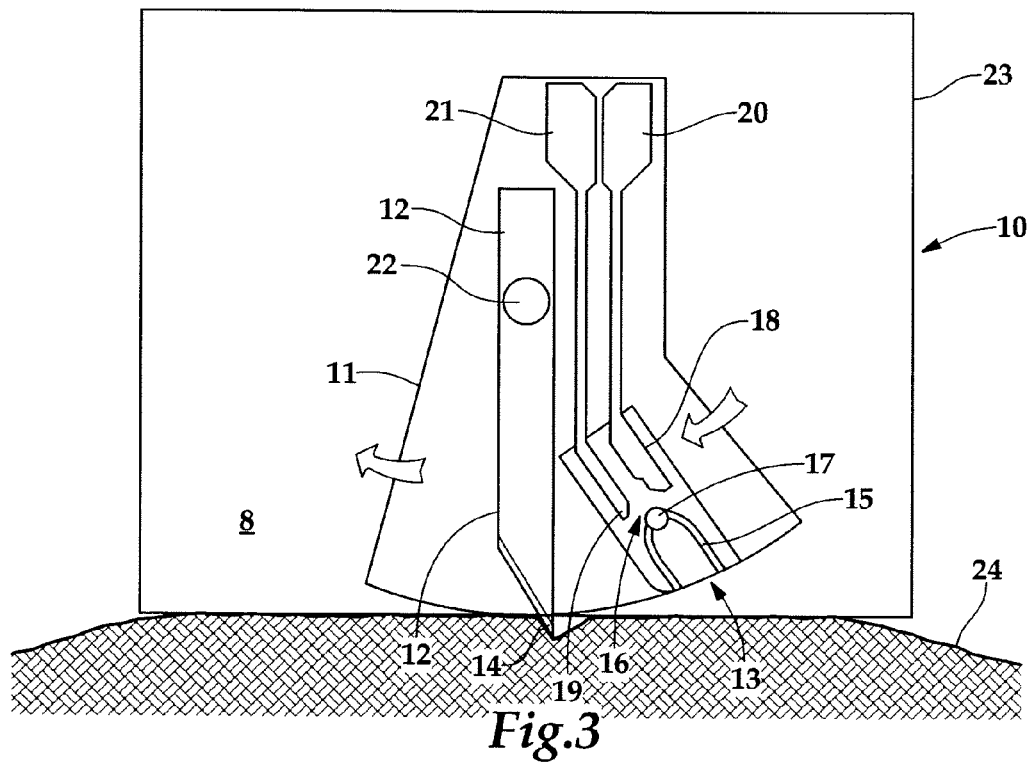
FIG. 3 is a side view of the apparatus shown in FIG. 2 as the arm rotates from the first position to a second position with the lance extended and lancing a site.

Referring now to FIG. 3, the arm 11 is between the first position and the second position. The penetration end 14 of the lance 12 extends beyond the outer periphery 23 of the housing 8 to cut the skin 24 to a predetermined depth and create a lance site. The lance site on the skin 24 allows a liquid sample 25 (see FIG. 4) to form near the lance site.

Figure 4:
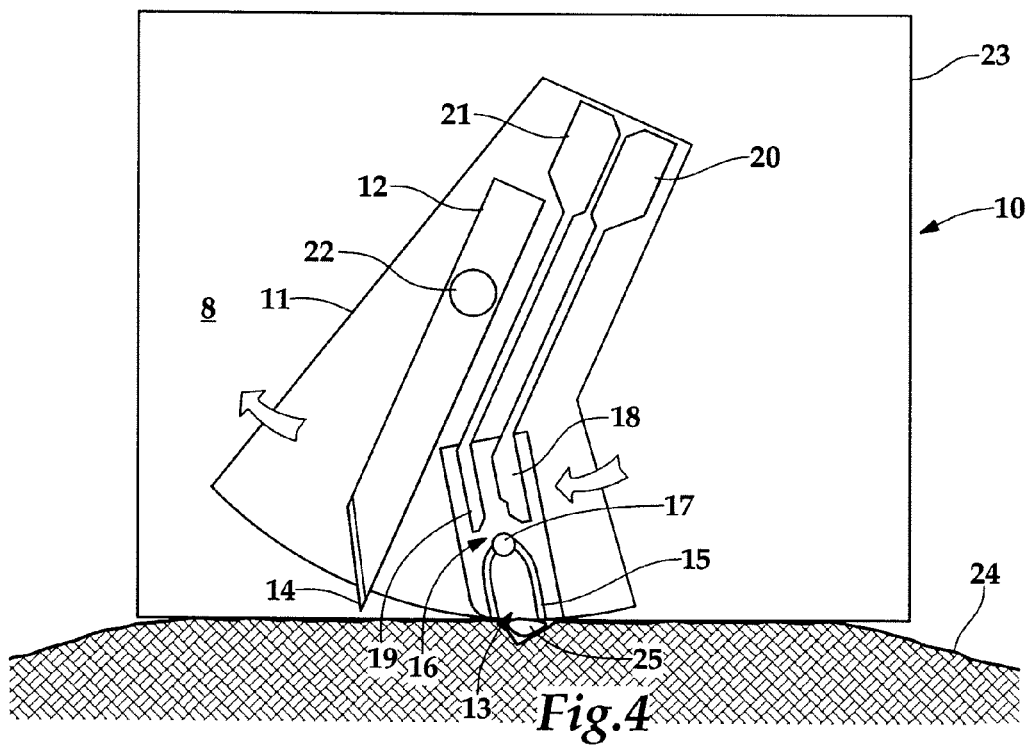
FIG. 4 is a side view of the apparatus of FIG. 3 with the arm in the second position with the lance in the housing and a collection area positioned at the lance site.

Referring now to FIG. 4, the arm 11 rotated to the second position. The second position is a predefined stopping point for the pendulum 11 that positions the collection area 13 over the lance site to collect the sample 25. At the second position, the penetration end 14 of lance 12 is within the housing 8. The collection area 13 is in substantially the same location of the skin 24 at which the penetration end 14 of the lance 12 created the lance site. When the sample collection area 13 is over the lance site in the skin 24, the liquid sample 25 is able to move into the sample collection area 13 via capillary channel 15, or be contacted by other sample structure used instead of the collection area. FIGS. 1-4 illustrate the collection area 13 spaced apart from the lance 12. In some embodiments, the lance penetration end 14 and collection area 13 are colocated.

A rotating lance, such as for example illustrated in FIGS. 1-4, can be combined with structure for storing a plurality of disposable sensors, in for example a cartridge. Referring now to FIG. 5A a top view of such an apparatus 40 for lancing skin and positioning a disposable sensor to collect a liquid sample. The apparatus 40 has a housing 42 with an outer periphery 44. The apparatus 40 comprises a rotatable arm 46 (or disc 46) having a lance 48 and a nest 50 for receiving a disposable sensor. The housing 42 contains cartridge 52 comprising a stack of disposable sensors. The disc 46 is adapted to rotate three hundred and sixty degrees within the housing 42. In FIG. 5A, the cartridge 52 is sealed against the disc 46 and the lance 48 is stored.

Referring now to FIG. 5B, arm 46 is rotated ninety degrees clockwise from the position shown in FIG. 5A. The nest 50 is located under the cartridge 52 so that a new sensor can be loaded. The sensor is pushed into the nest 50 by spring pressure from within the cartridge 52. The lance 48 is still located within the housing 42 and the lance drive, e.g., a spring, is cocked.

Referring now to FIG. 5C, the disc 46 is rotated ninety degrees clockwise from the position shown in FIG. 5B. The lance 48 is extended beyond the outer periphery 44 of the housing 42 to puncture the skin. A sensor 53 ejected from cartridge 52 is shown on nest 50. The cartridge 52 comprising the stack of disposable sensors has not been moved and is again sealed against the disc 46.

Referring now to FIG. 5D, the movable disc 46 is rotated ninety degrees clockwise from the position shown in FIG. 5C. The lance 48 is stored within the housing 42. The sensor 53 positioned on nest 50 is positioned so that it is in substantially the same location as the lance site created by the lance 48. In this position of the disc 46, sensor 53 collects the liquid sample.

The disc 46 is rotated ninety more degrees clockwise to eject the now used sensor 53 and store the nest 50. The disc 46 is then in the position shown in FIG. 5A.

Further details concerning disposable sensors and device for dispensing sensors is found in U.S. Pat. Nos. D456,514; 6,316,264; 5,854,074; 5,810,199; and 5,632,410, all of which are incorporated herein by reference in their entirety.

While the invention is susceptible to various modifications and alternative forms, specific embodiments thereof have been shown by way of example in the drawings herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

What is claimed is:

1. An apparatus for lancing skin, collecting a liquid sample and determining an analyte concentration of a fluid sample, the apparatus comprising:
    a housing sized to be handheld and having an outer periphery;
    a lance for lancing skin, the lance being fully within the outer periphery of the housing in the first predefined position, the lance extending beyond the outer periphery of the housing in the second predefined position so as to create a lance site in skin of a user, the lance being fully within the outer periphery after creating the lance site in the skin of the user; and
    a sample-collection area being positioned within an effective range of the lance site to collect the liquid sample, the sample-collection area being distinct and separate from the lance;
    a fluid-testing area being in fluid communication with the sample-collection area, the fluid-testing area assisting in determining the analyte concentration of the fluid sample, the fluid-testing area and the sample-collection area being located in a general fixed relation to the lance, wherein the lance and the sample-collection area simultaneously move in a single generally downwardly direction in forming the lance site and collecting the liquid sample after forming the lance site.

2. The apparatus of claim 1, wherein the sample-collection area overlaps at least a portion of the lance site when collecting the fluid sample.

3. The apparatus of claim 1, wherein the fluid-testing area includes a biosensor.

4. The apparatus of claim 3, wherein the biosensor is an electrochemical biosensor.

5. The apparatus of claim 3, wherein the biosensor is an optical biosensor.

6. The apparatus of claim 1, wherein the sample-collection area includes a capillary channel for collecting the fluid sample and moving the sample to the fluid-testing area, the fluid-testing area including a reagent for producing a reaction with an analyte in the sample indicative of the analyte concentration of the fluid sample.

7. The apparatus of claim 1, wherein the lance includes a generally flat blade end.

8. The apparatus of claim 1, wherein the fluid-testing area includes glucose oxidase.

9. The apparatus of claim 3, wherein the fluid-testing area includes glucose.

10. A method of lancing the skin, collecting a liquid sample and determining an analyte concentration of a fluid sample, the method comprising the acts of:
    providing an apparatus having a housing with an outer periphery, the apparatus including a lance, a sample-collection area and a fluid-testing area, the lance being fully within the outer periphery of the housing in the first predefined position, the sample-collection area and fluid-testing area being distinct and separate from the lance, the fluid-testing area and sample-collection area being in fluid communication therewith, the fluid-testing area and the sample-collection area being located in a generally fixed position relative to the lance, the fluid-testing area assisting in determining the analyte concentration of the fluid sample;
    positioning the apparatus at a site to be lanced;
    moving the lance from the first predefined position to the second position extending beyond the outer periphery of the housing to create a lance site in skin of a user;
    after creating the lance site, moving the lance from the lance site such that the lance is fully within the outer periphery of the housing;
    positioning the sample-collection area within an effective range of the lance site;
    collecting the liquid sample in the sample-collection area; and
    determining the analyte concentration of the fluid sample, wherein the lance and the sample-collection area simultaneously move in a single generally downwardly direction in forming the lance site and collecting the liquid sample after forming the lance site.

11. The method of claim 10, wherein the sample-collection area overlaps at least a portion of the lance site.

12. The method of claim 10, wherein the fluid-testing area includes a biosensor.

13. The method of claim 12, wherein the biosensor is an electrochemical biosensor.

14. The method of claim 12, wherein the biosensor is an optical biosensor.

15. The method of claim 10, wherein the sample-collection area includes a capillary channel for collecting the sample and moving the sample to the fluid-testing area, the fluid-testing area having a reagent for producing a reaction with an analyte in the sample indicative of the analyte concentration in the fluid sample.

16. The method of claim 10, wherein the lance includes a generally flat blade end.

17. The method of claim 10, wherein the fluid-testing area includes glucose oxidase.

18. The method of claim 12, wherein the fluid-testing area includes glucose oxidase.

* * * * *